US012029391B2

(12) United States Patent
Kim et al.

(10) Patent No.: US 12,029,391 B2
(45) Date of Patent: Jul. 9, 2024

(54) MICRO ROBOT DRIVING APPARATUS (71) Applicant: KOREA INSTITUTE OF MEDICAL MICROROBOTICS, Gwangju (KR)

(72) Inventors: Chang-Sei Kim, Gwangju (KR); Jongoh Park, Gyeonggi-do (KR); Eunpyo Choi, Gwangju (KR); Byungjeon Kang, Gwangju (KR); Jayoung Kim, Daejeon (KR); Gwangjun Go, Gwangju (KR); Kim Tien Nguyen, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 490 days.

(21) Appl. No.: 17/295,573

(22) PCT Filed: Feb. 7, 2020

(86) PCT No.: PCT/KR2020/001778
§ 371 (c)(1),
(2) Date: May 20, 2021

(87) PCT Pub. No.: WO2020/171443
PCT Pub. Date: Aug. 27, 2020

(65) Prior Publication Data
US 2022/0015612 A1 Jan. 20, 2022

(30) Foreign Application Priority Data

Feb. 19, 2019 (KR) .................. 10-2019-0019446
Apr. 4, 2019 (KR) .................. 10-2019-0039836
Feb. 7, 2020 (KR) .................. 10-2020-0014849

(51) Int. Cl.
A61B 1/00 (2006.01)
G05D 1/00 (2024.01)
(Continued)

(52) U.S. Cl.
CPC ........... *A61B 1/00158* (2013.01); *G05D 1/10* (2013.01); *H01F 7/20* (2013.01); *A61B 1/041* (2013.01)

(58) Field of Classification Search
CPC ............... A61B 1/00158; A61B 1/041; A61B 2017/22084; A61B 17/22; A61B 34/72;
(Continued)

(56) References Cited

U.S. PATENT DOCUMENTS
2007/0260105 A1 11/2007 Uchiyama et al.

FOREIGN PATENT DOCUMENTS
KR 10-2011-0000779 A 1/2011
KR 10-1647020 B1 8/2016
(Continued)

OTHER PUBLICATIONS
International Search Report from corresponding PCT Application No. PCT/KR2020/001778, dated Jun. 29, 2020.
(Continued)

Primary Examiner — Brian P Sweeney
(74) Attorney, Agent, or Firm — Harness, Dickey & Pierce, P.L.C.

(57) ABSTRACT

The present invention relates to a micro robot driving apparatus which can increase the intensity of magnetic field generation in a driving area of a micro robot by attaching a magnetic shield unit to an electromagnetic drive coil unit for driving the micro robot, or locally focus a magnetic field through the combination of two electromagnets, and a system using the same. According to the present invention, there is an effect that driving the micro robot injected into the body may be controlled by increasing a magnetic field generation intensity in the region of interest or focusing the magnetic field.

12 Claims, 7 Drawing Sheets (51) Int. Cl.
  *H01F 7/20* (2006.01)
  *A61B 1/04* (2006.01)
(58) Field of Classification Search
  CPC .. A61B 2017/00345; A61B 2034/2065; A61B 2034/303; A61B 2034/731; A61B 2090/374; A61B 2090/376; A61B 34/73; A61B 17/00; G05D 1/10; H01F 7/20; B25J 7/00; B25J 9/12
  See application file for complete search history.

(56) References Cited

FOREIGN PATENT DOCUMENTS

| KR | 101647020 B1 * | 8/2016 |
| KR | 10-2017-0085900 A | 7/2017 |
| KR | 20170085900 A * | 7/2017 |
| KR | 10-2017-0099232 A | 8/2017 |

OTHER PUBLICATIONS

About Magnetic Shield (Overview), Naver Blog, Oct. 10, 2016, 7 pages. (URL https://blog.naver.com/bh_tech/220832446286).

* cited by examiner

MICRO ROBOT DRIVING APPARATUS

CROSS-REFERENCE TO RELATED APPLICATIONS

This application is a national phase entry of PCT Application No. PCT/KR2020/001778, filed on Feb. 7, 2020, which claims benefit of Korean Patent Application Nos. 10-2019-0019446, filed on Feb. 19, 2019, 10-2019-0039836, filed on Apr. 4, 2019 and 10-2020-0014849, filed on Feb. 7, 2020. The entire disclosure of the applications identified in this paragraph are incorporated herein by references.

FIELD

The present disclosure has been made according to project number HI19C0642 under the support of the Ministry of Health and Welfare, the research management institution for the above project is the Korea Health Industry Development Institute, the title of the research business is "Development of Technology and Commercialization for Medical Micro-robots", the title of the research project is "Common Basis Technology Development Center for Commercialization of Medical Micro-robots", the host organization thereof is the Korea Institute of Medical Micro-robotics, and the research period thereof is Jun. 12, 2019 to Dec. 31, 2022.

The present invention relates to a micro robot driving apparatus, and more particularly, to a micro robot driving apparatus which can increase the intensity of magnetic field generation in a driving area of a micro robot by attaching a magnetic shield unit to an electromagnetic drive coil unit for driving the micro robot, or locally focus a magnetic field through the combination of two electromagnets, and a system using the same.

BACKGROUND ART

Minimal invasive procedures using micro robots as an operation method which minimizes the incision site to reduce the suffering of a patient, and shortens a recovery period have recently been researched a lot.

A method for controlling a motion of a micro robot can be divided into an external driving method and a self-driving method. The self-driving method includes a method of performing propulsion by using a pressure of gas generated by a mutual chemical reaction between an external fluid and a micro robot body, a method of using a biological propulsion force such as a bacterial movement, and the like. However, the self-driving method has a limit that it is difficult to apply the self-driving method to the inside of the human body due to a low control degree of freedom, a low control precision, and a chemical/biological toxicity problem for driving the micro robot.

A micro robot driving method using a magnetic field is a representative external driving method with high safety in the human body, and can be classified as a method using a permanent magnet or an electromagnetic driving coil apparatus. In particular, compared to the method using the permanent magnet, the micro robot control method using an electromagnetic driving coil is one of fields which have various application ranges and are most actively researched due to an advantage of being able to precisely control an intensity and a direction of the magnetic field by controlling current applied to a coil. In particular, a lot of researches for propelling the micro robot by using an external magnetic field or driving the micro robot for treatment have been performed, and a majority of the researches are performed on a 2D plane or a research capable of simply moving in a 3D space is primarily performed. A part or the entirety of a medical device is configured by a magnet without a battery or a separate driver so as to be controlled by using the magnetic field. When the battery or the driver is replaced with the magnet, the medical device can be designed in a small size. A medical device of which size is minimized enables minimum invasive procedures. This has an advantage in that the incision site is minimized during the operation to reduce the suffering and a recovery period of a patient. The systems can align the magnet in the body or derive movement by arranging a magnet outside the body or using an electromagnetic driving system having a cylindrical structure form such as MRI in order to align a medical device including the magnet positioned inside the body or derive movement. The medical device with the magnet can be controlled by a magnetic field generating apparatus provided outside. The used magnetic field generating apparatus includes a permanent magnet and an electromagnet. The permanent magnet can be driven by controlling a distance between the medical device and the permanent magnet, and a direction of the magnetic field. However, in this case, there is a problem in that there is a limit in a motion and a control speed of the medical device.

The medical device driven by the electromagnet can be controlled by the magnetic field generated by applying current to a coil fixed and arranged outside. In this case, when an intensity and the direction of the current applied to each coil is controlled, desired driving of the medical device can be implemented. It is easier to control the medical device in the method using the electromagnet than in the method using the permanent magnet, and the motion of the medical device can be rapidly controlled according to characteristics of the coil. However, as the medical device is further, spaced apart from the electromagnetic driving apparatus, the magnetic field applied to the medical device is sharply reduced. In this case, there is a problem in that the electromagnetic driving apparatus should apply a lot of current to the coil according to a spacing distance in order to control the medical device. More specifically, in the conventional electromagnetic driving apparatus, the coil is fixed and arranged in forming the magnetic field on a table on which a subject lies. Therefore, at the time of diagnosing the subject, the spacing distance between the coil and the medical device varies depending on a body type of the subject and a diagnosis site. Controlling a current amount applied to the coil by considering the intensity of the magnetic field which varies depending on the distance is inefficient in terms of control precision and power.

Further, in order to increase the magnetic force, the electromagnet can be configured by a combination of the coil and a magnetic core. As mentioned above, in order to increase the magnetic force, as the electromagnet (coil and magnetic core) closer to the subject, a large magnetic force is exerted.

In order to apply the micro robot to the human body and drive the micro robot in the human body, a sufficient size of magnetic field intensity is required. However, to this end, there is a limit that a size and a weight of an electromagnetic driving coil for generating the magnetic field should also increase. Therefore, for commercialization, a development of an electromagnetic driving coil capable of generating a magnetic field having a sufficient size to drive the micro robot, and miniaturized is required.

In addition, when driving the micro robot injected into the body is controlled by generating the magnetic force in a form in which the magnetic fields of the respective electromagnets overlap spatially based on an arrangement structure of multiple electromagnets, the magnetic force can be applied only unidirectionally, and as a result, a location of the micro robot injected into the body should be accurately recognized in order to move the micro robot to a desired location, and there is a problem in that it is significantly difficult to accurately recognize the location of the micro robot or a nano robot in the human body.

SUMMARY

Technical Problem

The present invention is contrived to solve the above-described problem, and an object of the present invention is to provide a micro robot driving apparatus including a miniaturized electromagnetic driving coil capable of generating a magnetic field having a size sufficient to drive a micro robot, and a system using the same.

Another object of the present invention is to provide a micro robot driving apparatus which can effectively control the drive of a micro robot injected into the body by focusing a magnetic field on a desire location in a local area by combining two electromagnets, and a system using the same.

Yet another object of the present invention is to provide a micro robot driving apparatus including a miniaturized electromagnet, which combines two electromagnets and includes a magnetic shielding unit to focus a magnetic field on a desired location in a local area and generate a magnetic field having a size sufficient to drive a micro robot, and a system using the same.

The objects of the present invention are not limited to the above-mentioned objects, and other objects and advantages of the present invention that are not mentioned can be understood by the following description, and will be more clearly understood by embodiments of the present invention. Further, it will be readily appreciated that the objects and advantages of the present invention can be realized by means and combinations shown in the claims.

Technical Solution

According to an aspect of the present invention, a micro robot driving apparatus and a system using the same are apparatuses for electromagnetically driving a micro robot including a magnet, and provided is a micro robot driving apparatus including: a magnetic shielding electromagnetic driving coil unit including a magnetic shielding electromagnetic driving coil module constituted by a coil winding unit and a magnetic shielding unit; and a power supply unit generating an induced magnetic field by applying magnetization current to the magnetic shielding electromagnetic driving coil module, in which the magnetic shielding unit is configured to surround a single end of the coil winding unit.

The magnetic shielding electromagnetic driving coil module includes a core unit made of a soft magnet material and the core unit is positioned at an opposite end to the coil winding unit at which the magnetic shielding unit is positioned.

A length ratio of the coil winding unit and the magnetic shielding unit may be 4 to 1:1 to 3, and according to a preferred implementation example, the length ratio of the coil winding unit and the magnetic shielding unit may be 4:1, 3:1, 3:2, 4:3, or 1:1, and more preferably, the length ratio of the coil winding unit and the magnetic shielding unit is 4:3.

The micro robot driving apparatus may include: a control unit controlling the magnetic shielding electromagnetic driving coil unit and the power supply unit, and a magnetic shielding region adjusting unit adjusting a region surrounding the coil winding unit by adjusting a length of the magnetic shielding unit, and the magnetic shielding region adjusting unit is controlled by the control unit.

In the used system, the magnetic shielding electromagnetic driving coil unit may include a plurality of magnetic shielding electromagnetic driving coil modules.

According to another aspect of the present invention, provided is a micro robot driving apparatus for electromagnetically driving a micro robot including a magnet, which includes: a first electromagnet with a hollow; a second electromagnet disposed in a hollow of the first electromagnet, and applied with current to form a second magnetic field; and a power supply unit applying the current to the electromagnet to generate a magnetic field, in which a first magnetic field formed by the first electromagnet and a second magnetic field formed by the second electromagnet overlap with each other to form an overlapping magnetic field in a predetermined region.

A direction of current which flows on the first electromagnet and a direction of current which flows on the second electromagnet are opposite directions to each other.

The first electromagnet may be configured in a circular coil form and the second electromagnet may be configured by a solenoid coil.

According to yet another aspect of the present invention, provided is a micro robot driving apparatus for electromagnetically driving a micro robot including a magnet, which includes: a first electromagnet with a hollow; a second electromagnet disposed in the hollow of the first electromagnet and including a magnetic shielding unit; and a power supply unit applying the current to the electromagnet to generate a magnetic field, in which a first magnetic field formed by the first electromagnet and a second magnetic field formed by the second electromagnet overlap with each other to form an overlapping magnetic field in a predetermined region, and the magnetic shielding unit is positioned on an opposite end to the first electromagnet.

The micro robot driving apparatus may include: a control unit controlling the second electromagnet including the magnetic shielding unit and the power supply unit; and a magnetic shielding region adjusting unit adjusting a length of the magnetic shielding unit to adjust a region surrounding the second electromagnet, in which the magnetic shielding region adjusting unit is controlled by the control unit.

A length ratio of the second electromagnet and the magnetic shielding unit may be 4 to 1:1 to 3, and according to a preferred implementation example, the length ratio of the second electromagnet and the magnetic shielding unit may be 4:1, 3:1, 3:2, 4:3, or 1:1, and more preferably, the length ratio of the second electromagnet and the magnetic shielding unit is 4:3.

Advantageous Effects

According to the present invention, the micro robot driving apparatus and the system using the same according to the present invention increase the magnetic field generation intensity in a region of interest by mounting the magnetic shielding unit of the electromagnetic driving coil unit, or focus the magnetic field through the combination of two electromagnets to control driving of the micro robot injected into the body. Further, when the magnetic field is focused through the combination of two electromagnets, a location on which the magnetic field is focused can be accurately controlled, so that the location of the micro robot injected into the body can be targeted to a specific location without prior recognition. Further, a coil for generating the magnetic field can be miniaturized, and a micro robot driving apparatus (or driving system) constituted by multiple coils can be miniaturized.

BEST MODE

A micro robot driving apparatus for electromagnetically driving a micro robot including a magnet includes: a magnetic shielding electromagnetic driving coil unit including a magnetic shielding electromagnetic driving coil module constituted by a coil winding unit and a magnetic shielding unit; and a power supply unit generating an induced magnetic field by applying magnetization current to the magnetic shielding electromagnetic driving coil module, in which the magnetic shielding unit is configured to surround a single end of the coil winding unit.

DETAILED DESCRIPTION

The above-mentioned objects, features, and advantages will become more apparent from the detailed description described below with reference to the drawings. Therefore, those skilled in the art to which the present invention pertains may easily practice a technical idea of the present invention. Further, in describing the present invention, in the case in which it is decided that a detailed description of a well-known technology associated with the present invention may unnecessarily make the gist of the present invention unclear, the detailed description will be omitted.

Throughout the specification, unless explicitly described to the contrary, any part "comprising or including" any component will be understood to imply the inclusion of any other elements but not the exclusion of any other elements. In addition, the term "unit" disclosed in the specification means a unit that processes at least one function or operation, and the unit may be implemented by hardware or software or a combination of hardware and software. Furthermore, unless differently indicated in this specification or apparently refurbished in a context describing the present invention, "a or an", "one", and similar related words may be used as a meaning including both singular and plural forms.

Further, it should be understood that, when it is described that a component is "connected to" or "accesses" another component, the component may be directly connected to or access the other component or a third component may be present therebetween. In contrast, it should be understood that, when it is described that a component is "directly connected to" or "directly accesses" another component, it is understood that no element is present between the element and another element. Meanwhile, other expressions describing the relationship of the components, that is, expressions such as "between" and "directly between" or "adjacent to" and "directly adjacent to" should be similarly interpreted.

A micro robot driving method using a magnetic field is a representative external driving method with high safety in the human body, and may be classified as a method using a permanent magnet or an electromagnetic driving coil apparatus. In particular, compared to the method using the permanent magnet, the micro robot control method using an electromagnetic driving coil is a field which has various application ranges and is most actively researched due to an advantage of being able to precisely control an intensity and a direction of the magnetic field by controlling current applied to a coil.

In the present invention, a human body implantable medical device refers to all human body implantable medical devices that are partially or entirely surgically or medically designed, and may be a medical device inserted into the human body even after a surgical procedure to maintain life, or includes all medical devices which may be temporarily inserted into the human body for the surgical procedure or diagnosis.

In the present invention, the micro robot may be classified into a mechanical/electronic micro robot including a permanent magnet or an elongated body as a magnetic body of a millimeter scale such as a vascular robot and an active capsule endoscope and a polymer/cell-based micro robot including magnetic nanoparticles as a magnetic body of a micro/nano scale size, such as a micro carrier for DDS, a micro scaffold for delivery of a cell therapy agent, and a nanorobot, and a macrophage robot, and may include other types of micro robots. In particular, in the present invention, the human body implantable medical device may include a magnetic body which is magnetized in the magnetic field, and for example, the permanent magnet may be used as the magnetic body.

Hereinafter, a preferred embodiment of the present invention will be described in detail with reference to the accompanying drawings together.

Figure 1:
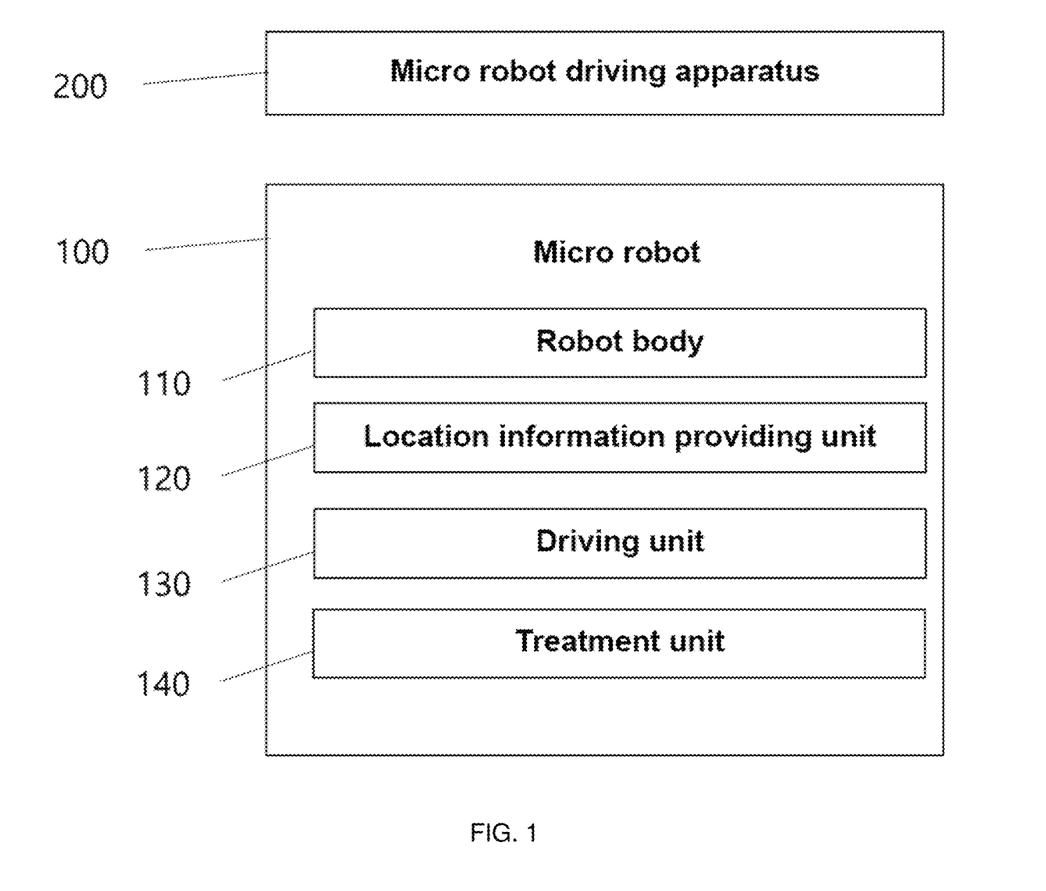
FIG. 1 illustrates an example of a micro robot system according to an embodiment of the present invention.

FIG. 1 illustrates an example of a micro robot system according to an embodiment of the present invention.

As illustrated in FIG. 1, a micro robot driving system according to the present invention includes a micro robot 100; and a magnetic shielding electromagnetic driving apparatus which is a micro robot driving apparatus 200 for driving the micro robot 100.

The micro robot 100 may be configured to include a magnet so as to have a random magnetization direction. The micro robot 100 performs a rotation motion and/or a motion in a random direction by a magnetic field generated by the micro robot driving apparatus 200.

The micro robot 100 may be configured to include a robot body. The micro robot may be configured only by the robot body, and may be configured to further include at least one component of a camera module, a location information providing unit, a driving unit, a treatment unit, a robot control unit, a data transmission/reception unit, and a wireless power receiving unit.

The robot body 110 as a part for defining the outside of the micro-robot may be manufactured in a size to move inside a subject or inside the blood vessel. Further, a leading portion of the robot body 110 may be manufactured in a streamlined shape so that a fiction with a blood flow is small. Further, the leading portion of the robot body 110 may include a fragment collector for collecting treatment fragments which are generated during blood vessel treatment.

A location information providing unit 120 is provided at a predetermined portion inside the robot body, and provides location information in the blood vessel of the robot body to the outside. For example, the location information providing unit 120 is provided as an intravascular ultrasound (IVUS) generating ultrasounds, and compares an ultrasound image generated by inputting the micro robot into the blood vessel and a blood vessel image through the existing preoperative image (CT or MRI) to provide a location of the micro robot to the outside.

The micro robot may not include the location information providing unit. In the case of the micro robot not including the location information providing unit, the location of the micro robot in the human body may be provided to the outside through an external image imaging apparatus using radiation or the magnetic field, such as X-ray or MRI.

A driving unit 130 is provided at a predetermined portion of the robot body, and moves the robot body inside the blood vessel. The micro robot may receive driving force by the magnetic field.

A treatment unit 140 as a part that is provided at a predetermined portion of the robot body and treats a vascular disease is configured to include a micro drill that physically treats the vascular disease, a drug tank and a drug sprayer that chemically treats the vascular disease, a center holder that fixes the robot body inside the blood vessel at the time of treating the blood vessel, and a fragment collector that collects treatment fragments generated during treatment.

Meanwhile, in an embodiment of the present invention, the micro drill is provided at the leading portion of the robot body as a physical treatment method, but in addition to the micro drill, a scalpel, forceps, or scissors may be further provided to physically treat the vascular disease.

Further, a drug stored in the drug tank may be, for example, a drug that includes a drug carrier, a ligand formed outside the drug carrier, and an enzyme for decomposition, and targets CTO or blood clots.

The micro robot driving apparatus 200 of the present invention may be a magnetic shielding electromagnetic driving apparatus adopting a magnetic shielding unit shielding the magnetic field generated in the electromagnetic driving apparatus.

Hereinafter, the magnetic shielding electromagnetic driving apparatus which is the micro robot driving apparatus 200 of the present invention will be described in detail.

Figure 2:
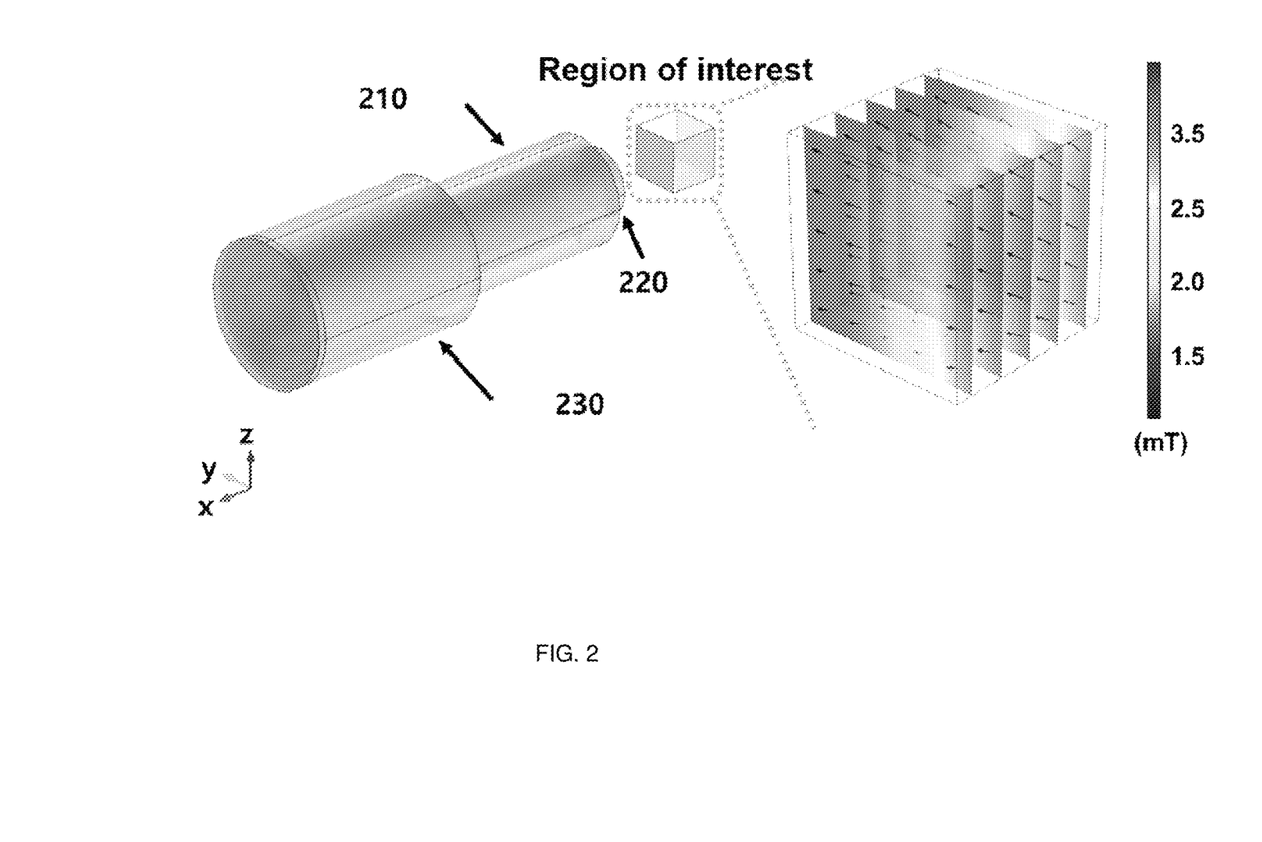
FIG. 2 illustrates a schematic diagram of a magnetic shielding electromagnetic driving coil apparatus for increasing an intensity of a magnetic field as an embodiment of the present invention.

FIG. 2 illustrates a schematic diagram of a magnetic shielding electromagnetic driving apparatus for increasing an intensity of a magnetic field as an embodiment of the present invention.

The magnetic shielding electromagnetic driving apparatus which is the micro robot driving apparatus 200 of FIG. 2 may include at least one of a magnetic shielding electromagnetic driving coil unit constituted by one or a plurality of magnetic shielding electromagnetic driving coil modules, a power supply unit applying magnetization current to the magnetic shielding electromagnetic driving coil module and generating an induced magnetic field, and a control unit controlling the magnetic shielding electromagnetic driving coil unit and the power supply unit.

In addition, the magnetic shielding electromagnetic driving coil may be configured to include at least one of a coil winding unit 210, a core unit 220, a magnetic shielding unit 230, and a magnetic shielding area adjusting unit (not illustrated).

The coil winding unit 210 may be configured in a form in which a coil configured by a copper wire or an aluminum wire coated with an insulating material is wound in a continuous ring shape.

The core unit 220 may be configured to be inserted into the coil winding unit 210.

The core unit 220 is made of a soft magnetic body material that is magnetized by an external magnetic field. The soft magnetic body material refers to a magnetic body which is strongly magnetized even by applying a small external magnetic field and has a small residual magnetization.

The magnetic shielding unit 230 is configured to prevent the magnetic field generated from the electromagnetic coil from escaping from the area of the magnetic shielding unit 230. The magnetic shielding unit 230 is positioned outside the coil winding unit 210 and may be configured to surround the entirety or a part of the coil winding unit 210. Preferably, the magnetic shielding unit 230 may be configured in a form to surround a single end of the coil in the coil winding unit 210. The magnetic shielding unit 230 is made of the soft magnetic material that is magnetized by the external magnetic field.

The material of the soft magnetic body is a soft magnetic body selected from a group consisting of pure iron, electromagnetic soft iron, silicon steel, permalloy (Ni—Fe system), Co—Fe-based alloy (ex. VACOFULX™), sendust (sendust, Fe—Al—Si system), Mn—Zn ferrite, Ni—Zn ferrite, Fe-based amorphous alloy, Co-based amorphous alloy, Fe-based thin film and multi-layered film, Co-based thin film and multi-layered film, and Ni-based thin film and multi-layered film but is not limited thereto.

The magnetic shielding area adjusting unit adjusts a length of the magnetic shielding unit 230 to adjust a magnetic shielding area surrounding the coil winding unit. The magnetic shielding area adjusting unit is controlled through the control unit of the micro robot driving apparatus 200 and adjusts the magnetic shielding area to adjust a magnetic field intensity through magnetic shielding. For example, the control unit controls the magnetic shielding area adjusting unit by setting a length of the magnetic shielding unit 230 in which the intensity of the magnetic field becomes largest through the magnetic shielding to thereby control the magnetic field generated by the magnetic shielding electromagnetic driving apparatus to be largest. As another example, the control unit controls the magnetic shielding area through the length of the magnetic shielding unit 230 corresponding to an intensity of the input magnetic field so as to allow the magnetic shielding electromagnetic driving apparatus to operate by the intensity of the input magnetic field to thereby control the magnetic shielding electromagnetic driving apparatus to operate at the intensity of the input magnetic field.

A region of interest may be positioned in a direction of the coil winding unit not surrounded by the magnetic shielding unit 230. The region of interest may be defined as a region at which the micro robot moved by applying the magnetic field generated by the magnetic shielding electromagnetic driving apparatus is positioned or a region for controlling the micro robot through the magnetic shielding electromagnetic driving apparatus.

As illustrated in FIG. 2, an arrow in a region acquired by enlarging the region of interest of FIG. 2 indicates the direction of the magnetic field and each color indicates the size of the magnetic field.

Hereinafter, the analytical verification of the magnetic shielding electromagnetic driving apparatus by mounting the magnetic shielding unit will be described.

Figure 3:
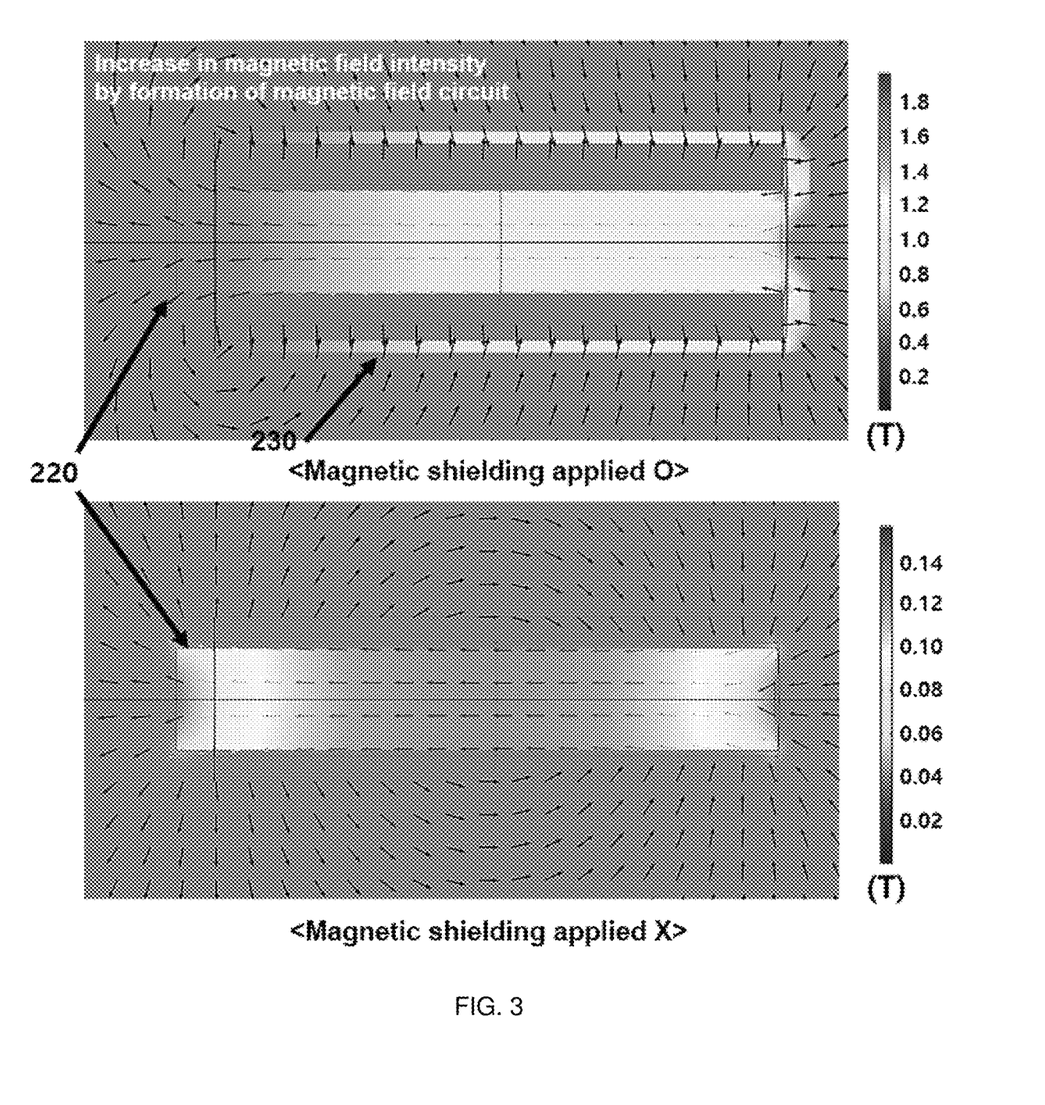
FIG. 3 is a diagram illustrating a direction and an intensity of the magnetic field according to whether to apply a magnetic shielding unit as an embodiment of the present invention.

FIG. 3 is a diagram illustrating a direction and an intensity of the magnetic field according to whether to apply a magnetic shielding unit as an embodiment of the present invention.

A magnetic field flow is verified through FEM analysis according to whether the magnetic shielding unit 230 is mounted on an electromagnetic coil into which the pure iron of the diagram of FIG. 3 is inserted. First, a lower figure of FIG. 3 illustrates a magnetic field flow of a general electromagnetic driving apparatus not adopting the magnetic shielding unit. When the flow of the magnetic field in the core unit 220 is formed from a right direction to a left direction of the core unit 220, the flow of the magnetic field is formed from the left of the core unit 220 to the right of the core unit 220 outside the core unit 220. In addition, it is verified that when current of 1A is applied, a magnetic field of up to appropriately 0.14 T is generated when the magnetic shielding is not applied. On the contrary, an upper figure of FIG. 3 illustrates a magnetic field flow of the magnetic shielding electromagnetic driving apparatus adopting the magnetic shielding unit 230. The flow of the magnetic field in the core unit 220 is similar to that when the magnetic shielding unit is not applied in overall. However, the magnetic field by the electromagnetic coil may not escape to the region to which the magnetic shielding unit is applied.

However, it is confirmed that when the current of 1A is applied, the magnetic field of up to approximately 1.9 T is generated when the magnetic shielding is applied. It can be seen that when the magnetic shielding unit 230 is applied, a magnetic field is generated, which is approximately 10 times or more larger than a case where the magnetic shielding unit 230 is not applied. Such a difference occurs when as the magnetic shielding unit 230 is mounted, the magnetic field generated from the electromagnetic coil may not escape outside and locked in the magnetic shielding unit 230, and is the same as a kind of magnetic field circuit effect.

Figure 4:
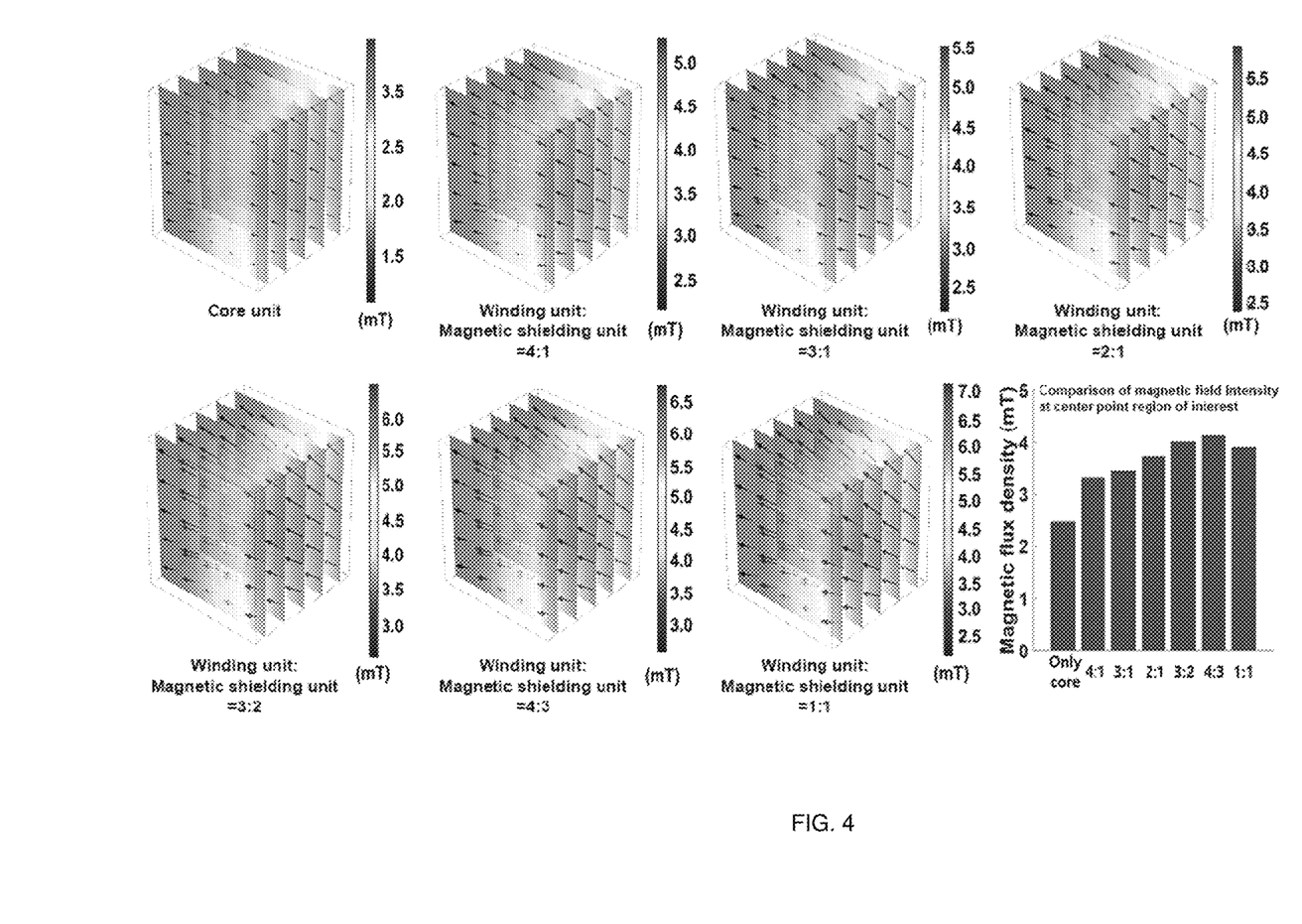
FIG. 4 illustrates a magnetic field intensity in a region of interest according to a length ratio for a coil winding unit and a magnetic shielding unit as an embodiment of the present invention.

FIG. 4 illustrates a magnetic field intensity in a region of interest according to a length ratio for a coil winding unit and a magnetic shielding unit as an embodiment of the present invention.

A role of the magnetic shielding unit is verified by checking the magnetic field flow by applying the magnetic shielding unit of FIG. 3.

In FIG. 4, in more detail, in order to quantitatively evaluate the effect of the magnetic shielding unit on the electromagnetic coil apparatus, the magnetic field intensity in the region of interest depending on a length ratio (4:1, 3:1, 2:1, 3:2, 4:3, or 1:1) of the coil winding unit and the magnetic shielding unit is compared through FEM analysis.

As illustrated in FIG. 4, it can be seen that when the magnetic shielding unit is not applied, the magnetic field intensity at a center point of the region of interest is approximately 2.5 mT.

It can be seen that when the magnetic shielding unit is applied, and a ratio of the length of the coil winding unit and the length of the magnetic shielding unit is 4:1, the magnetic field intensity at the center point of the region of interest is approximately 3.3 mT.

It can be seen that when the magnetic shielding unit is applied, and the ratio of the length of the coil winding unit and the length of the magnetic shielding unit is 3:1, the magnetic field intensity at the center point of the region of interest is approximately 3.5 mT.

It can be seen that when the magnetic shielding unit is applied, and the ratio of the length of the coil winding unit and the length of the magnetic shielding unit is 2:1, the magnetic field intensity at the center point of the region of interest is approximately 3.6 mT.

It can be seen that when the magnetic shielding unit is applied, and a ratio of the length of the coil winding unit and the length of the magnetic shielding unit is 3:2, the magnetic field intensity at the center point of the region of interest is approximately 3.9 mT.

It can be seen that when the magnetic shielding unit is applied, and a ratio of the length of the coil winding unit and the length of the magnetic shielding unit is 4:3, the magnetic field intensity at the center point of the region of interest is approximately 4.1 mT.

It can be seen that when the magnetic shielding unit is applied, and a ratio of the length of the coil winding unit and the length of the magnetic shielding unit is 1:1, the magnetic field intensity at the center point of the region of interest is approximately 3.8 mT.

As in an experimental result, it can be seen that as the length of the magnetic shielding unit increases, the magnetic field intensity at the center point of the region of interest of the micro robot gradually increases. However, it can be seen that when the length of the magnetic shielding unit is equal to that of the coil winding unit (1:1), the magnetic field intensity at the center point of the region of interest of the micro robot decreases. This is an effect generated as the magnetic field which flows out from the end of the coil winding unit directly flows to the magnetic shielding unit by a magnetic field circuit effect.

Therefore, it can be seen that the magnetic field intensity is maximized by configuring the magnetic shielding unit in a form not to surround a partial end rather than configuring the magnetic shielding unit to surround the entirety of the coil winding unit.

It is confirmed that the magnetic field intensity in the region of interest through mounting of the magnetic shielding unit of the electromagnetic driving coil unit increases through the experimental result. As a result, when a principle in which the magnetic field generated in the region of interest increases is applied by applying the magnetic shielding unit to the coil, miniaturization and weight lightening of the coil may be implemented. Further, miniaturization and weight lightening of a micro robot driving apparatus constituted by multiple coils and a system including the same may also be implemented.

When the micro robot driving apparatus and the system including the same are miniaturized and weigh-lightened, there is an advantage in that it may become easy to apply the micro robot driving apparatus and the system including the same to actual clinical sites such as hospitals, medical centers, etc.

Figure 5:
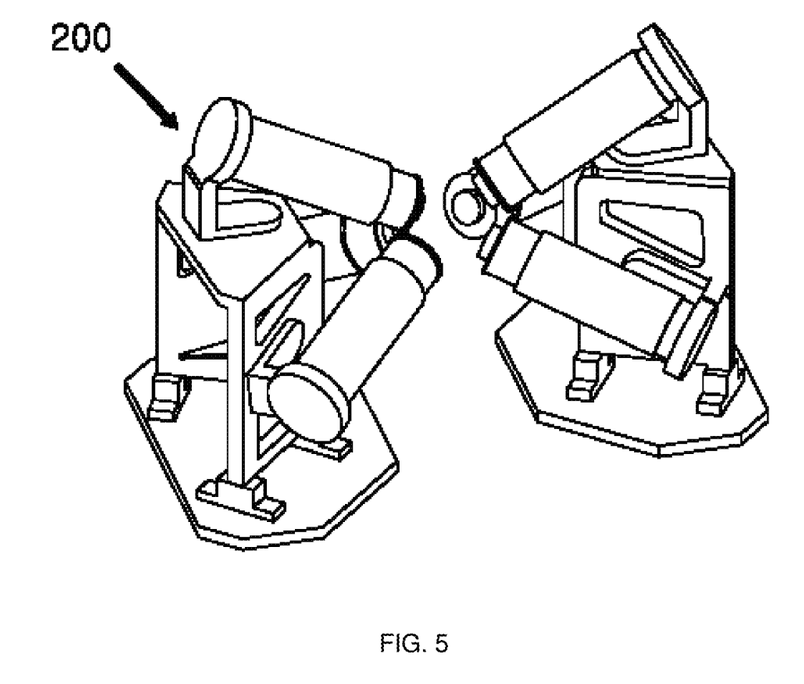
FIG. 5 illustrates an example of an electromagnetic coil apparatus for driving a micro robot using a magnetic shielding electromagnetic driving coil as an embodiment of the present invention.

FIG. 5 illustrates an example of an electromagnetic coil apparatus for driving a micro robot adopting a magnetic shielding unit as an embodiment of the present invention.

As illustrated in FIG. 5, the micro robot driving apparatus 200 may be configured through a combination/arrangement of a plurality of magnetic shielding electromagnetic driving coil units including the magnetic shielding unit.

Figure 6:
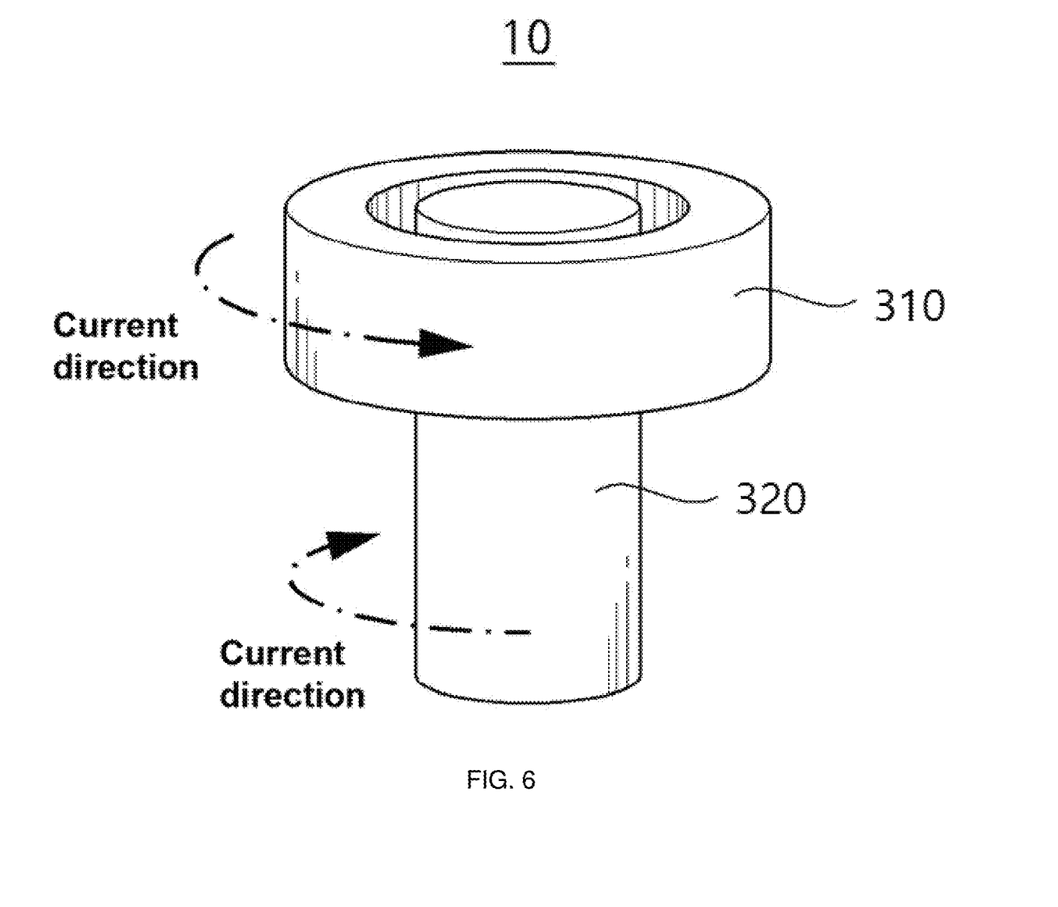
FIG. 6 illustrates an example in which two electromagnets for generating a magnetic field which is locally focused are combined in a micro robot driving apparatus as an embodiment of the present invention.
Figure 7:
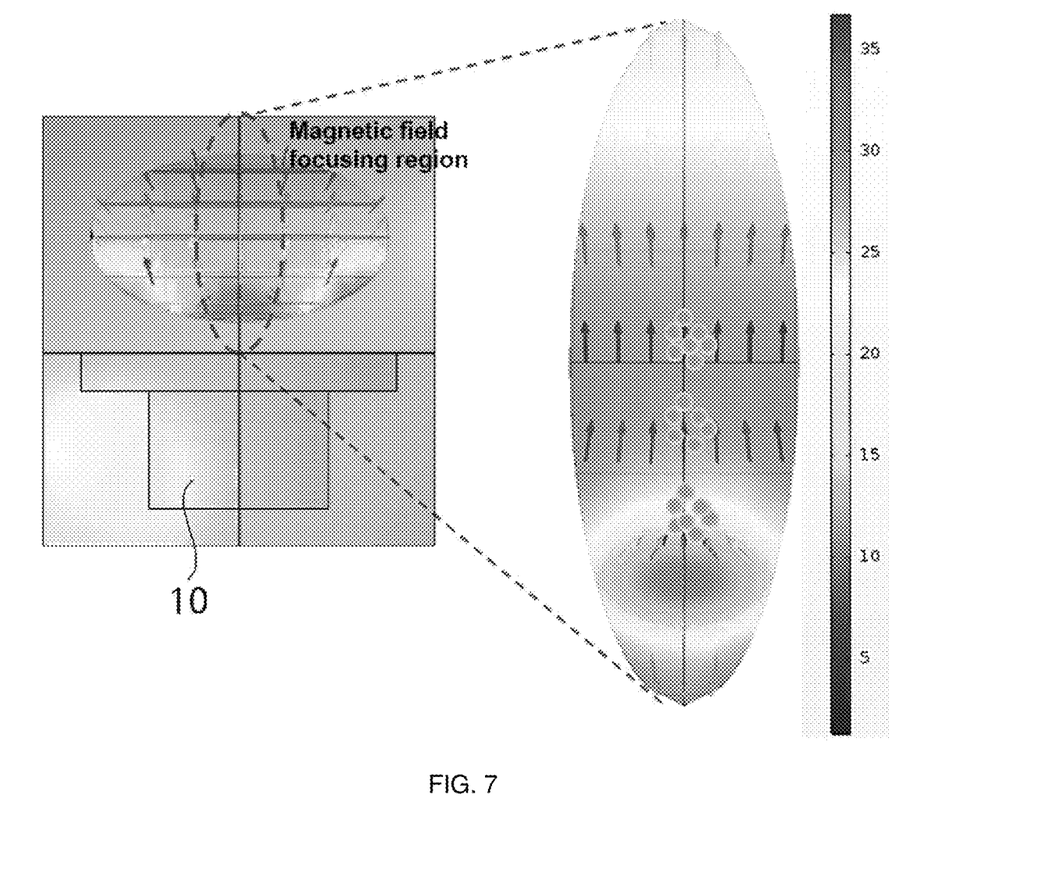
FIG. 7 is a diagram illustrating an area where the magnetic field locally focused through the combination of two electromagnets is generated according to the present invention.

FIG. 6 is a schematic diagram schematically illustrating an apparatus which may locally focus a magnetic field through a combination of two electromagnets according to an embodiment of the present invention and FIG. 7 is a diagram illustrating a magnetic field focus area formed by using the apparatus which may locally focus the magnetic field through the combination of two electromagnets.

Referring to FIGS. 6 and 7, an apparatus 300 capable of locally focusing the magnetic field through the combination of two electromagnets according to an embodiment of the present invention includes a first electromagnet 310 having a hollow and forming a first magnetic field by applying current, and a second electromagnet 320 disposed in the hollow of the first electromagnet and forming a second electromagnet by applying the current, and the first magnetic field formed by the first electromagnet and the second magnetic field formed by the second electromagnet overlap with each other to form an overlapping magnetic field of a predetermined region. A technical feature of the present invention is that the second electromagnet is disposed in the hollow of the first electromagnet to generate the overlapping magnetic field in the predetermined region, and an executer may appropriately select and apply diameters of the first and second electromagnets, a diameter of the hollow formed in the first electromagnet, a spacing distance between the surface of the hollow formed in the first electromagnet and an outer wall surface of the second electromagnet, etc., according to an applied human environment, a size of an applied diseased area, a size of the micro robot, a size and a direction of a desired generated magnetic field, etc.

In order to generate the focused magnetic field, directions of currents applied to the first and second electromagnets are opposite to each other, and the sizes of the currents may be set differently based on a location on which the magnetic field focuses. A location change of the magnetic field focusing is made in a direction of a central axis of the electromagnet, and a magnetic field equation having the current as a variable may be derived for the first and second electromagnets through the Maxwell theory. The sizes of the currents applied to the first and second electromagnets may be determined according to a desired magnetic field focusing location by combining the magnetic field equations of the first and second electromagnets. The currents required for the first and second electromagnets may be supplied through a power supplier.

The apparatus 300 capable of locally focusing the magnetic field through the combination of two electromagnets according to an embodiment of the present invention as one specific use example may be used as an apparatus for focusing the magnetic field on a local portion of the human body. By focusing the magnetic field on the local portion of the human body, driving a micro robot (not illustrated) injected into the body may be controlled. Here, the direction and a speed of the micro robot may be controlled by an electromagnetic field and the micro robot may have a hard magnet or soft magnet property in order to react to the electromagnetic field.

The micro robot may be a multicomponent assembly in which magnetic particles are partially introduced, and the multicomponent may be selected from various materials including biocompatible polymers, various drugs, proteins, cells, and the like without limitation.

As illustrated in the figure, the apparatus 300 capable of locally focusing the magnetic field through the combination of two electromagnets according to an embodiment of the present invention is configured in a form in which a first electromagnet 310 and a second electromagnet 320 are combined. The combination of the first electromagnet 310 and the second electromagnet 320 may be formed by a third support that does not have conductivity and does not interfere with magnetic field formation. The third support may be disposed in a scheme in which the third support is partially combined with the first electromagnet 310 and the second electromagnet 320 to fix the arrangement of the first electromagnet 310 and the second electromagnet 320, or disposed in a cover shape to cover outer surfaces of the first electromagnet 310 and the second electromagnet 320. Even any conventional known scheme of fixing the arrangement of the first and second electromagnets may also be used.

The first electromagnet 310 is configured in a circular coil form with the hollow, and the current is applied to the first electromagnet 310 to form the first magnetic field. Further, the second electromagnet 320 disposed in the first electromagnet 310 is configured by a solenoid coil, and the current is applied to the second electromagnet 320 to form the second magnetic field. In this case, as illustrated, a direction of current which flows on the first electromagnet 310 and a direction of current which flows on the second electromagnet 320 are set to opposite directions to each other.

As described above, the first electromagnet 310 and the second electromagnet 320 are unidirectionally combined and the currents applied to the respective electromagnets 310 and 320 are applied in opposite directions to each other, and as a result, the first magnetic field formed by the first electromagnet 310 and the second magnetic field formed by the second electromagnet 320 overlap with each other to form the overlapping magnetic field.

As illustrated in FIG. 7, the overlapping magnetic field formed by the first electromagnet 310 and the second electromagnet 320 focuses the magnetic force so that a value of the magnetic field may be formed to be high at a predetermined region, i.e., a desired location. Accordingly, according to the apparatus capable of locally focusing the magnetic field through the combination of two electromagnets according to the present invention, the magnetic force is focused on a desired location without using multiple electromagnet arrangement structures in order to control the micro robot injected into the body, thereby aligning the micro robot at a local location on which the magnetic force focuses.

The aforementioned present invention is not limited to the aforementioned embodiments and the accompanying drawings, and it will be obvious to those skilled in the technical field to which the present invention pertains that various substitutions, modifications, and changes may be made within the scope without departing from the technical spirit of the present invention.

INDUSTRIAL APPLICABILITY

The present invention relates to a micro robot driving apparatus, and more particularly, to a micro robot driving apparatus which can increase the intensity of magnetic field generation in a driving area of a micro robot by attaching a magnetic shield unit to an electromagnetic drive coil unit for driving the micro robot, or locally focus a magnetic field through the combination of two electromagnets, and a system using the same.

What is claimed is:

1. A micro robot driving apparatus for electromagnetically driving a micro robot including a magnet, the apparatus comprising:
   a magnetic shielding electromagnetic driving coil unit including a magnetic shielding electromagnetic driving coil module, wherein the magnetic shielding electromagnetic driving coil module is constituted by a coil winding-unit and a magnetic shielding unit configured to prevent the magnetic field generated from the coil;
   a power supply generating an induced magnetic field by applying magnetization current to the magnetic shielding electromagnetic driving coil module,
   a control unit controlling the magnetic shielding electromagnetic driving coil unit and the power supply; and
   a magnetic shielding region adjusting unit adjusting a region surrounding the coil winding unit by adjusting a length of the magnetic shielding unit,
      wherein the magnetic shielding unit is configured to surround a single end of the coil winding unit, and
      wherein the magnetic shielding adjusting unit is controlled by the control unit.

2. The micro robot driving apparatus of claim 1, wherein the magnetic shielding electromagnetic driving coil module includes a core unit made of a soft magnet material and the core unit is positioned at an opposite end to the coil winding unit at which the magnetic shielding unit is positioned.

3. The micro robot driving apparatus of claim 1, wherein a length ratio of the coil winding unit and the magnetic shielding unit is 4 to 1:1 to 3.

4. The micro robot driving apparatus of claim 1, wherein the magnetic shielding electromagnetic driving coil unit includes a plurality of magnetic shielding electromagnetic driving coil modules.

5. A micro robot driving system comprising:
   a micro robot including a magnet; and
   a micro robot driving apparatus controlling a location of the micro robot,
   wherein the micro robot driving apparatus includes
      a magnetic shielding electromagnetic driving coil unit including a magnetic shielding electromagnetic driving coil module wherein the magnetic shielding electromagnetic driving coil module is constituted by a coil and a magnetic shielding unit configured to prevent the magnetic field generated from the coil; and
      a power supply generating an induced magnetic field by applying magnetization current to the magnetic shielding electromagnetic driving coil module,
      a control unit controlling the magnetic shielding electromagnetic driving coil unit and the power supply; and
      a magnetic shielding region adjusting unit adjusting a region surrounding the coil winding unit by adjusting a length of the magnetic shielding unit,
         wherein the magnetic shielding unit is configured to surround a single end of the coil winding unit, and
         wherein the magnetic shielding region adjusting unit is controlled by the control unit.

6. The micro robot driving system of claim 5, wherein the magnetic shielding electromagnetic driving coil module includes a core unit made of a soft magnet material and the core unit is positioned at an opposite end to the coil winding unit at which the magnetic shielding unit is positioned.

7. The micro robot driving system of claim 5, wherein a length ratio of the coil winding unit and the magnetic shielding unit is 4:3.

8. The micro robot driving system of claim 5, wherein the magnetic shielding electromagnetic driving coil unit includes a plurality of magnetic shielding electromagnetic driving coil modules.

9. A micro robot driving apparatus for electromagnetically driving a micro robot including a magnet, the apparatus comprising:
   a first electromagnet with a hollow;
   a second electromagnet disposed in the hollow of the first electromagnet and including a magnetic shielding unit configured to prevent the magnetic field generated from the coil;
   a power supply applying the current to the electromagnet to generate a magnetic field,
   a control unit controlling the second electromagnet including the magnetic shielding unit and the power supply; and
   a magnetic shielding region adjusting unit adjusting a length of the magnetic shielding unit to adjust a region surrounding the second electromagnet,
      wherein a first magnetic field formed by the first electromagnet and a second magnetic field formed by the second electromagnet overlap with each other to form an overlapping magnetic field in a predetermined region,
      wherein the magnetic shielding unit is positioned on an opposite end to the first electromagnet and
      wherein the magnetic shielding region adjusting unit is controlled by the control unit.

10. The micro robot driving apparatus of claim 9, wherein a length ratio of the second electromagnet and the magnetic shielding unit is 4 to 1:1 to 3.

11. A micro robot driving system comprising:
   a micro robot including a magnet; and
   a micro robot driving apparatus controlling a location of the micro robot,
   wherein the micro robot driving apparatus includes
      a first electromagnet with a hollow;
      a second electromagnet disposed in the hollow of the first electromagnet and including a magnetic shielding unit configured to prevent the magnetic field generated from the coil;
      a power supply applying the current to the electromagnet to generate a magnetic field,
      a control unit controlling the second electromagnet including the magnetic shielding unit and the power supply; and
      a magnetic shielding region adjusting unit adjusting a length of the magnetic shielding unit to adjust a region surrounding the second electromagnet,
         wherein a first magnetic field formed by the first electromagnet and a second magnetic field formed by the second electromagnet overlap with each other to form an overlapping magnetic field in a predetermined region,
         wherein the magnetic shielding unit is positioned on an opposite end to the first electromagnet, and
         wherein the magnetic shielding region adjusting unit is controlled by the control unit.

12. The micro robot driving system of claim 11, wherein a length ratio of the second electromagnet and the magnetic shielding unit is 4 to 1:1 to 3.

\* \* \* \* \*